United States Patent [19]
Fitton et al.

[11] Patent Number: 5,439,815
[45] Date of Patent: Aug. 8, 1995

[54] RESTRICTOCIN-LIKE RIBOTOXIN ANALOGUES COMPRISING ONLY ONE CYSTEINE AVAILABLE FOR COVALENT LINKAGE TO A PARTNER

[75] Inventors: John E. Fitton, Buxton; David Timms, Macclesfield, both of England

[73] Assignee: Imperial Chemical Industries plc, London, United Kingdom

[21] Appl. No.: 912,740

[22] Filed: Jul. 13, 1992

[30] Foreign Application Priority Data

| Jul. 24, 1991 | [GB] | United Kingdom | 9115999 |
| Jul. 24, 1991 | [GB] | United Kingdom | 9116000 |
| Jul. 24, 1991 | [GB] | United Kingdom | 9116001 |
| Jul. 24, 1991 | [GB] | United Kingdom | 9116002 |
| Jul. 24, 1991 | [GB] | United Kingdom | 9116011 |
| Apr. 6, 1992 | [GB] | United Kingdom | 9207488 |
| Apr. 16, 1992 | [GB] | United Kingdom | 9208397 |

[51] Int. Cl.⁶ .................. C12N 9/22; C12N 15/55; C12N 1/21; C12N 5/10; C12N 1/15
[52] U.S. Cl. .................. 435/199; 435/69.1; 435/172.3; 435/320.1; 435/252.3; 435/240.1; 435/254.11; 536/23.2; 536/23.4; 935/10; 935/14
[58] Field of Search .................. 530/388.2, 388.8, 350, 530/387.3, 402, 403, 404; 435/69.1, 199, 320.1, 240.1, 252.3, 243, 69.2; 536/23.2, 23.4; 424/94.5, 94.1; 514/2; 935/14, 33, 34, 44

[56] References Cited

U.S. PATENT DOCUMENTS

| 3,104,204 | 9/1963 | Olson et al. | 424/117 |
| 3,104,208 | 9/1963 | Olson et al. | 435/71.1 |
| 4,340,535 | 7/1982 | Voisin et al. | 435/172.3 |
| 4,753,894 | 6/1988 | Frankel et al. | 435/240.27 |

FOREIGN PATENT DOCUMENTS

| 355460 | 2/1990 | European Pat. Off. . |
| 3266986 | 11/1991 | Japan . |
| WO88/07578 | 10/1988 | WIPO . |
| WO89/01782 | 3/1989 | WIPO . |
| WO90/12874 | 11/1990 | WIPO . |

OTHER PUBLICATIONS

Hird et al. (1990) in Genes & Cancer, Carney et al (ed) New York: Wiley & Sons, pp. 183–189.
Osband et al (1990) Immunol. Today, 11:193–195.
Harris et al. (1993) Tibtech II:42–44.
Oka et al., Nucleic Acids Research, vol. 18, No. 7, p. 1897, 1990; "Complete nucleotide sequence of cDNA for . . .".
Orlandi et al., Cancer Immunology Immunotherapy, vol. 26, p. 114–120, 1988; "Immunoconjugate generation between . . .".
Conde et al., Journal of Cellular Biochemistry, Supp. 10B, abstract G83, p. 77, 1986; "Immunotoxins generated . . .".
Lyons et al., Protein Engineering, vol. 3, No. 8, pp. 703–708, 1990; "Site–specific attachment to recombinant antibodies . . .".
Better et al., The Journal of Biological Chemistry, vol. 267, No. 234, 1992; "Activity of Recombinant Mitogillin . . .".

(List continued on next page.)

Primary Examiner—Robert A. Wax
Assistant Examiner—G. E. Bugaisky
Attorney, Agent, or Firm—Nixon & Vanderhye

[57] ABSTRACT

Ribotoxins, such as restrictocin, mitogillin and alpha–sarcin which do not contain a cysteine for linkage to antibodies for immunotoxin production need to be modified for such linkage without compromising biological activity. Protein analogues of such native ribotoxins are provided in which both the analogue and the native ribotoxin can cleave only a single phosphodiester bond of 28S rRNA in a 60S ribosomal subunit and in which the analogue comprises only one cysteine available from covalent linkage to a partner, such as an antibody, which cysteine is not present in the native ribotoxin. Especially preferred analogues are restrictocin Cys 13, Cys 82, Cys 106 and Cys 110 and restrictocin Cys 150––Gly151. Corresponding DNA sequences, vectors, host cells, immunotoxins and pharmaceutical compositions are also claimed.

6 Claims, No Drawings

OTHER PUBLICATIONS

Munoz et al., Biochemical and Biophysical Research Communications, vol. 173, No. 2, pp. 554–560, 1990.

Wawrzynczak et al., European Journal of Biochemistry, vol. 196, pp. 203–209, 1991; "Biochemical, cytotoxic . . .".

Stirpe et al., FEBS Letters, vol. 195, No. 1, 2, pp. 1–8, 1986; "Ribosome–inactivating proteins up to date".

Carter et al., Science, vol. 237, pp. 394–399, 1987; "Engineering Enzyme Specificity by 'Substrate–Assisted Catalysis'".

Ljungquist et al., European Journal of Biochemistry, vol. 186, pp. 557–561, 1989; "Thiol–directed immobilization . . .".

Scott et al., JNCI, vol. 79, No. 5, 1987; "An Immunotoxin Composed of a Monoclonal Antitransferrin Receptor . . .".

Arruda et al., Journal of Experimental Medicine, vol. 172, pp. 1529–1532, 1990; "*Aspergillus fumigatus* Allergen I . . .".

Yang et al, Gembank, EMBL databases; accession #'s M65257, M55508; May 20, 1991; Sequence encoding restrictocin.

Bernhard et al, Enhanced Potency of Antibody Conjugates With Toxin Analogs Of Gelonin, Brip and Mitogillin, Program and Abstracts Third International Symposium of Immunotoxins, Jun. 19–21, 1992.

Better et al, Generation of Potent Immunoconjugates from Microbially Produced Fab', F(ab')2, and antibody–toxin gene fusions, Program and Abstracts Third International Symposium On Immunotoxins, Jun. 19–21, 1992.

Brigotti et al, Effect of α–sarcin and ribosome–inactivating proteins on the interaction of elongation factors with ribosomes, Biochem. J. vol. 257, 1989, pp. 723–727.

Conde et al, The Aspergillus toxin restrictocin is a suitable cytotoxic agent for generation of immunoconjugates with monoclonal antibodies directed against human carcinoma cells, Eur. J. Biochem., vol. 178, 1989, pp. 795–802.

Conde et al, Protein Toxins That Catalytically Inactivate Ribosomes From Eukaryotic Microorganisms Studies On The Mode Of Action Of Alpha Sarcin, Mitogillin And Restrictocin: Response To Alpha Sarcin Antibodies, FEMS Microbiology Letters, vol. 4, 1978, pp. 349–355.

Endo et al, The Site of Action α–Sarcin on Eurkaryotic Ribosomes—The Sequence at the α–Sarcin Cleavage Site in 28 S Ribosomal Ribonucleic Acid, The Journal of Biological Chemistry, vol. 257, No. 15, Aug. 1982, pp. 9054–9060.

Endo et al, The Ribonuclease Activity of the Cytotoxin α–Sarcin, The Journal of Biological Chemistry, vol. 258, No. 4, Issue of Feb. 25, 1983, pp. 2662–2667.

Fando et al, The Mode Of Action Of Restriction And Mitogillin On Eukaryotic Ribosomes—Inhibition of brain protein synthesis, cleavage and sequence of the ribosomal RNA fragment; J. Biochem., vol. 149, 1985, pp. 29–34.

Fernandez–Luna et al, Complete Amino Acid Sequence of the Aspergillus Cytrotoxin Mitogillin Biochemistry, vol. 24, 1985, pp. 861–867.

Gavilanes et al, Chemical and Spectroscopic Evidence on the Homology of Three Antitumor Proteins: α–Sarcin, Mitogillin, and Restrictocin, Journal of Protein Chemistry, vol. 2, No. 3, 1983, pp. 251–261.

Hatfull et al, Preparation of Heavy–atom Derivatives Using Site–directed Mutagenesis, J. Mol. Biol., vol. 208, 1989, pp. 661–667.

Henze et al., Expression of the Chemically Synthesized Coding Region for the Cytotoxin α–sarcin in *Escherichia coli* using a Secretion Cloning Vector, Eur. J. Biochem, vol. 192, 1990, pp. 127–131.

Hobden et al, The Mode of Action of Alpha Sarcin and a Novel Assay of the Puromycin Reaction, Biochem. J., vol. 170, 1978, pp. 57–61.

Lamy et al, Isolation and Nucleotide Sequence of the Aspergillus Restrictus Gene Coding for the Ribonucleolytic Toxin Restrictocin and its Expression in *Aspergillus nidulans:* The Leader Sequence Protects Producing Strains From Suicide, Nucleic Acids Research, vol. 19, No. 5, 1001–1006 (1991).

Lopez–Otin et al, The Primary Structure of the Cytotoxin Restictocin, Eur. J. Biochem. 143, (1984), pp. 621–634.

Lyons et al, Site–specific Attachment to Recombinant Antibodies Via Introduced Surface Cysteine Residues, Protein Engineering, vol. 3, No. 8, 1990, pp. 703–708.

Miller et al, The Ribosomes of *Aspergillus giganteus* are Sensitive to the Cytotoxic action of α–sarcin, FEB 05666, vol. 229, No. 2, 1988, pp. 388–390.

(List continued on next page.)

OTHER PUBLICATIONS

Munoz et al, Fractionation of the Ribosome Inactivating Protein Preparations with Triazine Dyes, Biochemical and Biophysical Research Communications, vol. 173, No. 2, 1990, pp. 554–560.

Olson et al, Alpha Sarcin, A New Antitumor Agent, Applied Microbiology, vol. 13, No. 3, 1965, pp. 314–321.

Olson et al, Alpha Sarcin, A New Antitumor Agent, Applied Microbiology, vol. 13, No. 3, 1965, pp. 322–326.

Orlandi et al, Immunoconjugate Generation Between the Ribosome Inactivating Protein Restrictocin and an Anti-human Breast Carinoma MAB, Cancer Immunol. Immunother. vol. 26, 1988, pp. 114–120.

Martinez del Pozo et al, Conformational Study of the Antitumor Protein α–Sarcin, Biochimica et Biophysica Acta vol. 953, 1988, pp. 280–288.

Rodriguez et al, Amino Acid Sequence homologies in Alfa–Sarcin, Restrictocin and Mitogillin, Biochemical and Biophysical Research Communications, vol. 108, No. 1, 1982, pp. 315–321.

Sacco et al, The Primary Structure of the Cytotoxin α–Sarcin, The Journal of Biological Chemistry, vol. 2, No. 9, 1983, pp. 5811–5818.

Sanz et al, Sensitivity of Thermoacidophilic Archaebacteria to α–sarcin, FEBS 1487, vol. 171, No. 1, 1984, pp. 63–66.

Schindler et al, Specific Cleavage of Ribosomal RNA caused by Alpha Sarcin, Nucleic Acids Research, vol. 4, No. 4, 1977, pp. 1097–1111.

Singh et al, Effects of Thiolation on the Immunoreactivity of the Ribosome–inactivating Protein Gelonin, Biochem. J., vol. 263, 1989, pp. 417–423.

Sperti et al, Alpha-Sarcin Impairs the N-Glycosidase Activity of Ricin on Ribosomes, Biochemical and Biophysical Research Communications, vol. 160, No. 2, 1989, pp. 857–861.

Wool, The Mechanism of Action of the Cytotoxic Nuclease α–sarcin and its use to Analyse Ribosome Structure, TIBS, 1984, pp. 14–17.

SEQUENCE LISTING ( 1 ) GENERAL INFORMATION:

( i i i ) NUMBER OF SEQUENCES: 48

( 2 ) INFORMATION FOR SEQ ID NO:1:

( i ) SEQUENCE CHARACTERISTICS:
        ( A ) LENGTH: 38 bases
        ( B ) TYPE: nucleic acid
        ( C ) STRANDEDNESS: single
        ( D ) TOPOLOGY: linear ( x i ) SEQUENCE DESCRIPTION: SEQ ID NO:1:

CCCTCAGCTG CAGCTACTTG GACTTGYATC AAYCARCA                      3 8

( 2 ) INFORMATION FOR SEQ ID NO:2:

( i ) SEQUENCE CHARACTERISTICS:
        ( A ) LENGTH: 51 bases
        ( B ) TYPE: nucleic acid
        ( C ) STRANDEDNESS: single
        ( D ) TOPOLOGY: linear ( x i ) SEQUENCE DESCRIPTION: SEQ ID NO:2:

CACCGACGTC GACTATTATT ARTGRS W RCA CAGNCGCAGR TCRCCYTGRT T        5 1

( 2 ) INFORMATION FOR SEQ ID NO:3:

( i ) SEQUENCE CHARACTERISTICS:
        ( A ) LENGTH: 41 bases
        ( B ) TYPE: nucleic acid
        ( C ) STRANDEDNESS: single
        ( D ) TOPOLOGY: linear ( x i ) SEQUENCE DESCRIPTION: SEQ ID NO:3:

AATTCGAGCT CGCCCGGGGA TCCTGCAGCT ACTTGGACTT G                     4 1

( 2 ) INFORMATION FOR SEQ ID NO:4:

( i ) SEQUENCE CHARACTERISTICS:
        ( A ) LENGTH: 45 bases
        ( B ) TYPE: nucleic acid
        ( C ) STRANDEDNESS: single
        ( D ) TOPOLOGY: linear ( x i ) SEQUENCE DESCRIPTION: SEQ ID NO:4:

CCAAGCTTGG GTTGCAGGTC GACTATTATT AGTGGCTACA CAGTC                4 5

( 2 ) INFORMATION FOR SEQ ID NO:5:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
                GTTTTCCCAG TCACGAC                                                17
```

( 2 ) INFORMATION FOR SEQ ID NO:6:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( x i ) SEQUENCE DESCRIPTION: SEQ ID NO:6:

```
                CAGGAAACAG CTATGAC                                                17
```

( 2 ) INFORMATION FOR SEQ ID NO:7:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( x i ) SEQUENCE DESCRIPTION: SEQ ID NO:7:

```
                ACGGGAATGG CAAGCTC                                                17
```

( 2 ) INFORMATION FOR SEQ ID NO:8:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
                GGTCTGGCTG TGCTTCG                                                17
```

( 2 ) INFORMATION FOR SEQ ID NO:9:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
                GAACCAGTGC GGGTAGC                                                17
```

( 2 ) INFORMATION FOR SEQ ID NO:10:

( i ) SEQUENCE CHARACTERISTICS:
        ( A ) LENGTH: 456 bases
        ( B ) TYPE: nucleic acid
        ( C ) STRANDEDNESS: single
        ( D ) TOPOLOGY: linear ( x i ) SEQUENCE DESCRIPTION: SEQ ID NO:10:

```
        GCT  ACT  TGG  ACT  TGT  ATC  AAC  CAA  CAG  CTG  AAT  CCC  AAG  ACA  AAC  AAA    48
        Ala  Thr  Trp  Thr  Cys  Ile  Asn  Gln  Gln  Leu  Asn  Pro  Lys  Thr  Asn  Lys
        1                  5                        10                       15

TGG  GAA  GAC  AAG  CGG  CTT  CTA  TAC  AGT  CAA  GCC  AAA  GCC  GAA  AGC  AAC    96
        Trp  Glu  Asp  Lys  Arg  Leu  Leu  Tyr  Ser  Gln  Ala  Lys  Ala  Glu  Ser  Asn
                           20                       25                       30

TCC  CAC  CAC  GCA  CCT  CTT  TCC  GAC  GGC  AAG  ACC  GGT  AGC  AGC  TAC  CCG   144
        Ser  His  His  Ala  Pro  Leu  Ser  Asp  Gly  Lys  Thr  Gly  Ser  Ser  Tyr  Pro
                  35                            40                       45

CAC  TGG  TTC  ACT  AAC  GGC  TAC  GAC  GGG  AAT  GGC  AAG  CTC  ATC  AAG  GGT   192
        His  Trp  Phe  Thr  Asn  Gly  Tyr  Asp  Gly  Asn  Gly  Lys  Leu  Ile  Lys  Gly
             50                       55                            60
```

| CGC | ACG | CCC | ATC | AAA | TTC | GGA | AAA | GCC | GAC | TGT | GAC | CGT | CCC | CCG | AAG | 240 |
| Arg | Thr | Pro | Ile | Lys | Phe | Gly | Lys | Ala | Asp | Cys | Asp | Arg | Pro | Pro | Lys | |
| 65 | | | | 70 | | | | | 75 | | | | | | 80 | |

| CAC | AGC | CAG | AAC | GGC | ATG | GGC | AAG | GAT | GAC | CAC | TAC | CTG | CTG | GAG | TTC | 288 |
| His | Ser | Gln | Asn | Gly | Met | Gly | Lys | Asp | Asp | His | Tyr | Leu | Leu | Glu | Phe | |
| | | | | 85 | | | | | 90 | | | | | 95 | | |

| CCG | ACT | TTT | CCA | GAT | GGC | CAC | GAC | TAT | AAG | TTT | GAC | TCG | AAG | AAA | CCC | 336 |
| Pro | Thr | Phe | Pro | Asp | Gly | His | Asp | Tyr | Lys | Phe | Asp | Ser | Lys | Lys | Pro | |
| | | | 100 | | | | | 105 | | | | | 110 | | | |

| AAG | GAA | GAC | CCG | GGC | CCA | GCG | AGG | GTC | ATC | TAT | ACT | TAT | CCC | AAC | AAG | 384 |
| Lys | Glu | Asp | Pro | Gly | Pro | Ala | Arg | Val | Ile | Tyr | Thr | Tyr | Pro | Asn | Lys | |
| | | 115 | | | | 120 | | | | | 125 | | | | | |

| GTG | TTT | TGC | GGC | ATT | GTG | GCC | CAT | CAG | CGG | GGG | AAT | CAA | GGC | GAT | CTG | 432 |
| Val | Phe | Cys | Gly | Ile | Val | Ala | His | Gln | Arg | Gly | Asn | Gln | Gly | Asp | Leu | |
| | 130 | | | | 135 | | | | | 140 | | | | | | |

| CGA | CTG | TGT | AGC | CAC | TAA | TAA | TAG | | | | | | | | | 456 |
| Arg | Leu | Cys | Ser | His | | | | | | | | | | | | |
| 145 | | | | | | | | | | | | | | | | |

( 2 ) INFORMATION FOR SEQ ID NO:11:

( i ) SEQUENCE CHARACTERISTICS:
    ( A ) LENGTH: 51 bases
    ( B ) TYPE: nucleic acid
    ( C ) STRANDEDNESS: single
    ( D ) TOPOLOGY: linear ( x i ) SEQUENCE DESCRIPTION: SEQ ID NO:11:

CAATCTAGAG GGTATTAATA ATGTTCCCAT TGGAGGATGA TTAAATGGTA C    51

( 2 ) INFORMATION FOR SEQ ID NO:12:

( i ) SEQUENCE CHARACTERISTICS:
    ( A ) LENGTH: 51 bases
    ( B ) TYPE: nucleic acid
    ( C ) STRANDEDNESS: single
    ( D ) TOPOLOGY: linear ( x i ) SEQUENCE DESCRIPTION: SEQ ID NO:12:

CATTTAATCA TCCTCCAATG GGAACATTAT TAATACCCTC TAGATTGAGC T    51

( 2 ) INFORMATION FOR SEQ ID NO:13:

( i ) SEQUENCE CHARACTERISTICS:
    ( A ) LENGTH: 21 bases
    ( B ) TYPE: nucleic acid
    ( C ) STRANDEDNESS: single
    ( D ) TOPOLOGY: linear ( x i ) SEQUENCE DESCRIPTION: SEQ ID NO:13:

CCGAAGCACT GCCAGAACGG C    21

( 2 ) INFORMATION FOR SEQ ID NO:14:

( i ) SEQUENCE CHARACTERISTICS:
    ( A ) LENGTH: 21 bases
    ( B ) TYPE: nucleic acid
    ( C ) STRANDEDNESS: single
    ( D ) TOPOLOGY: linear ( x i ) SEQUENCE DESCRIPTION: SEQ ID NO:14:

CACGACTATT GCTTTGACTC G    21

( 2 ) INFORMATION FOR SEQ ID NO:15:

( i ) SEQUENCE CHARACTERISTICS:
    ( A ) LENGTH: 21 bases
    ( B ) TYPE: nucleic acid ( C ) STRANDEDNESS: single
( D ) TOPOLOGY: linear ( x i ) SEQUENCE DESCRIPTION: SEQ ID NO:15:

CTGAATCCCT GCACAAACAA A                             21

( 2 ) INFORMATION FOR SEQ ID NO:16:

( i ) SEQUENCE CHARACTERISTICS:
( A ) LENGTH: 30 bases
( B ) TYPE: nucleic acid
( C ) STRANDEDNESS: single
( D ) TOPOLOGY: linear ( x i ) SEQUENCE DESCRIPTION: SEQ ID NO:16:

CTGTGTAGCC ACTGCGGTTA ATAATAGTCG                    30

( 2 ) INFORMATION FOR SEQ ID NO:26:

( i ) SEQUENCE CHARACTERISTICS:
( A ) LENGTH: 24 bases
( B ) TYPE: nucleic acid
( C ) STRANDEDNESS: single
( D ) TOPOLOGY: linear ( x i ) SEQUENCE DESCRIPTION: SEQ ID NO:26:

GCAGTTACTT GGACTTGCCT GAAC                          24

( 2 ) INFORMATION FOR SEQ ID NO:27:

( i ) SEQUENCE CHARACTERISTICS:
( A ) LENGTH: 63 bases
( B ) TYPE: nucleic acid
( C ) STRANDEDNESS: single
( D ) TOPOLOGY: linear ( x i ) SEQUENCE DESCRIPTION: SEQ ID NO:27:

GTTTCGTATT TGTTAGTTTT CGGGTTTTTC TGGTCGTTCA GGCAAGTCCA AGTAACTGCT 60

GCA                                                 63

( 2 ) INFORMATION FOR SEQ ID NO:31:

( i ) SEQUENCE CHARACTERISTICS:
( A ) LENGTH: 30 bases
( B ) TYPE: nucleic acid
( C ) STRANDEDNESS: single
( D ) TOPOLOGY: linear ( x i ) SEQUENCE DESCRIPTION: SEQ ID NO:31:

GTCCGCCGAA ACACTGCAAA GACGGTAACG                    30

( 2 ) INFORMATION FOR SEQ ID NO:34:

( i ) SEQUENCE CHARACTERISTICS:
( A ) LENGTH: 30 bases
( B ) TYPE: nucleic acid
( C ) STRANDEDNESS: single
( D ) TOPOLOGY: linear ( x i ) SEQUENCE DESCRIPTION: SEQ ID NO:34:

GGTCACGACT ACTGTTTCGA CTCTAAAAAA                    30

( 2 ) INFORMATION FOR SEQ ID NO:35:

( i ) SEQUENCE CHARACTERISTICS:
( A ) LENGTH: 30 bases
( B ) TYPE: nucleic acid
( C ) STRANDEDNESS: single
( D ) TOPOLOGY: linear ( x i ) SEQUENCE DESCRIPTION: SEQ ID NO:35:

ACCAGAAAAA CCCGTGTACT AACAAATACG    30

( 2 ) INFORMATION FOR SEQ ID NO:36:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( x i ) SEQUENCE DESCRIPTION: SEQ ID NO:36:

CTGTGCTCTC ACTGCGGTTG ATGGATCCCC    30

( 2 ) INFORMATION FOR SEQ ID NO:37:

( i ) SEQUENCE CHARACTERISTICS:
        ( A ) LENGTH: 50 bases
        ( B ) TYPE: nucleic acid
        ( C ) STRANDEDNESS: single
        ( D ) TOPOLOGY: linear ( x i ) SEQUENCE DESCRIPTION: SEQ ID NO:37:

GTAAAACTGG TTCCTCTTAC CCGCACTGGT TCACTAACGG TTACGACGGT    50

( 2 ) INFORMATION FOR SEQ ID NO:38:

( i ) SEQUENCE CHARACTERISTICS:
        ( A ) LENGTH: 50 bases
        ( B ) TYPE: nucleic acid
        ( C ) STRANDEDNESS: single
        ( D ) TOPOLOGY: linear ( x i ) SEQUENCE DESCRIPTION: SEQ ID NO:38:

AGTGAACCAG TGCGGGTAAG AGGAACCAGT TTTACCGTCA GACAGCGGAG    50

( 2 ) INFORMATION FOR SEQ ID NO:39:

( i ) SEQUENCE CHARACTERISTICS:
        ( A ) LENGTH: 55 bases
        ( B ) TYPE: nucleic acid
        ( C ) STRANDEDNESS: single
        ( D ) TOPOLOGY: linear ( x i ) SEQUENCE DESCRIPTION: SEQ ID NO:39:

GATCCGTCGA CTCAGTGAGA GCACAGTTTC AGTTCACCCT GGTTTTCTTT AGTGT    55

( 2 ) INFORMATION FOR SEQ ID NO:40:

( i ) SEQUENCE CHARACTERISTICS:
        ( A ) LENGTH: 36 bases
        ( B ) TYPE: nucleic acid
        ( C ) STRANDEDNESS: single
        ( D ) TOPOLOGY: linear ( x i ) SEQUENCE DESCRIPTION: SEQ ID NO:40:

AGGGTGAACT GAAACTGTGC TCTCACTGAG TCGACG    36

( 2 ) INFORMATION FOR SEQ ID NO:41:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( x i ) SEQUENCE DESCRIPTION: SEQ ID NO:41:

TTTGACTCGT GCAAACCCAA G    21

( 2 ) INFORMATION FOR SEQ ID NO:42:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( x i ) SEQUENCE DESCRIPTION: SEQ ID NO:42:

ACAAATTCGA CTCTTGTAAA CCGAAAGAAA          30

( 2 ) INFORMATION FOR SEQ ID NO:43:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:

GGATCCTGCA GCTACTTGGA CT          22

( 2 ) INFORMATION FOR SEQ ID NO:44:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: protein ( x i ) SEQUENCE DESCRIPTION: SEQ ID NO:44:

Ala Thr Trp Thr
1

( 2 ) INFORMATION FOR SEQ ID NO:45:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

CTGTGTAGCC ACTAATAATA GTCGAC          26

( 2 ) INFORMATION FOR SEQ ID NO:46:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: protein ( x i ) SEQUENCE DESCRIPTION: SEQ ID NO:46:

Leu Cys Ser His
1

( 2 ) INFORMATION FOR SEQ ID NO:47:

( i ) SEQUENCE CHARACTERISTICS:
        ( A ) LENGTH: 149 amino acids
        ( B ) TYPE: amino acid
        ( D ) TOPOLOGY: linear (ii) MOLECULE TYPE: peptide (xi) SEQUENCE DESCRIPTION: SEQ ID NO:47:

```
Ala Thr Trp Thr Cys Ile Asn Gln Gln Leu Asn Pro Lys Thr Asn Lys
 1           5                   10                  15

Trp Glu Asp Lys Arg Leu Leu Tyr Asn Gln Ala Lys Ala Glu Ser Asn
             20                  25                  30

Ser His His Ala Pro Leu Ser Asp Gly Lys Thr Gly Ser Ser Tyr Pro
         35                  40                  45

His Trp Phe Thr Asn Gly Tyr Asp Gly Asn Gly Lys Leu Ile Lys Gly
     50                  55                  60

Arg Thr Pro Ile Lys Phe Gly Lys Ala Asp Cys Asp Arg Pro Pro Lys
 65                  70                  75                  80

His Ser Gln Asn Gly Met Gly Lys Asp Asp His Tyr Leu Leu Glu Phe
                 85                  90                  95

Pro Thr Phe Pro Asp Gly His Asp Tyr Lys Phe Asp Ser Lys Lys Pro
             100                 105                 110

Lys Glu Asn Pro Gly Pro Ala Arg Val Ile Tyr Thr Tyr Pro Asn Lys
         115                 120                 125

Val Phe Cys Gly Ile Val Ala His Gln Arg Gly Asn Gln Gly Asp Leu
     130                 135                 140

Arg Leu Cys Ser His
145
```

(2) INFORMATION FOR SEQ ID NO:48:

(i) SEQUENCE CHARACTERISTICS:
(A) LENGTH: 150 amino acids
(B) TYPE: amino acid
(D) TOPOLOGY: linear (ii) MOLECULE TYPE: peptide (xi) SEQUENCE DESCRIPTION: SEQ ID NO:48:

```
Ala Val Thr Trp Thr Cys Leu Asn Asp Gln Lys Asn Pro Lys Thr Asn
 1           5                   10                  15

Lys Tyr Glu Thr Lys Arg Leu Leu Tyr Asn Gln Asn Lys Ala Glu Ser
             20                  25                  30

Asn Ser His His Ala Pro Leu Ser Asp Gly Lys Thr Gly Ser Ser Tyr
         35                  40                  45

Pro His Trp Phe Thr Asn Gly Tyr Asp Gly Asp Gly Lys Leu Pro Lys
     50                  55                  60

Gly Arg Thr Pro Ile Lys Phe Gly Lys Ser Asp Cys Asp Arg Pro Pro
 65                  70                  75                  80

Lys His Ser Lys Asp Gly Asn Gly Lys Thr Asp His Tyr Leu Leu Glu
                 85                  90                  95

Phe Pro Thr Phe Pro Asp Gly His Asp Tyr Lys Phe Asp Ser Lys Lys
             100                 105                 110

Pro Lys Glu Asn Pro Gly Pro Ala Arg Val Ile Tyr Thr Tyr Pro Asn
         115                 120                 125

Lys Val Phe Cys Gly Ile Ile Ala His Thr Lys Glu Asn Gln Gly Glu
     130                 135                 140

Leu Lys Leu Cys Ser His
145                 150
```

RESTRICTOCIN-LIKE RIBOTOXIN ANALOGUES COMPRISING ONLY ONE CYSTEINE AVAILABLE FOR COVALENT LINKAGE TO A PARTNER

BACKGROUND OF THE INVENTION

Ribotoxins are potent inhibitors of protein synthesis. They are believed to act as enzymes on the 28S rRNA of the eucaryotic ribosome and can be divided into two classes (Jiminez, A et al., 1985, Ann. Rev Microbiol., 39, 649–672, and Wool, I. G. et al., 1990, in Hill, W. E. et al. (ed.) The Ribosome Structure, Function & Evolution, American Society of Microbiology, Washington D.C., 203–214). Restrictocin, mitogillin and α-sarcin belong to the class which cleaves a single phosphodiester bond. Ricin belongs to the other class which cleaves an N-glycosidic linkage between base and ribose. The nucleotide sequence of the restrictocin gene has been described by Lamy, B. & Davies, J. in Nucleic Acids Research, 1991, 19, 1001–1006.

Immunotoxins are an example of a conjugate formed between two partners namely a toxin and an immunoglobulin or antibody. The partners are usually joined via a chemical linker but may be joined directly. Ribotoxins such as for example restrictocin may be used as the toxin component of immunotoxins, linked to the antibody via a variety of chemical linkers. Known methods involve derivatisation of the restrictocin with chemicals such as iminothiolane (although other derivatising agents, eg. N-succinimidyl-3-(2-pyridyldithio)-propionate (hereinafter abbrevated SPDP) may be used) to introduce a sulphydryl functionality and to form a disulphide cross-linked structure with an appropriately derivatised antibody.

Due to the inherent random nature of the chemical derivatisation at, primarily (although not necessarily solely), amino groups such as for example on the restrictocin molecule of which there are 17 including the alpha amino group, a heterogeneous product results comprising underivatised restrictocin, mono, di, tri etc derivatised molecules which may result in a complex product profile following conjugation to antibody (1,2,3 etc moles of restrictocin/mole antibody or, potentially, 1,2,3 etc moles of antibody/mole Restrictocin). Such a heterogeneous product undesirably produces batch to batch variability and reduced overall yield. Batch to batch variability is particularly undesirable in the pharmaceutical field where the product may be for example an immunotoxin wherein the antibody is selective for tumours and is used in cancer therapy.

In addition chemical derivatisation may derivatise residues close to the active site of the molecule so compromising biological activity of the derivatised toxin.

SUMMARY OF THE INVENTION

The present invention seeks to overcome these disadvantages by providing a protein analogue having a suitable sulphydryl functionality such that a specific amino acid residue in the protein sequence provides a single conjugation site at a defined position.

According to one aspect of the present invention there is provided a protein analogue of a native ribotoxin in which both the protein analogue and the native ribotoxin can cleave only a single phosphodiester bond of 28S rRNA in a 60S ribosomal subunit and in which the protein analogue comprises only one cysteine available for covalent linkage to a partner said cysteine not being present in the native ribotoxin.

The term "can cleave a single phosphodiester bond of 28S rRNA in a 60S ribosomal subunit" as used herein relates to the extremely selective action of the class of ribotoxins typified by restrictocin, mitogillin and alpha-sarcin (Wool, I. G., Jan 1984, Trends Biochem. Sci. 14–17). Thus protein analogues of the present invention substantially retain the biological activity of ribotoxins such as restrictocin, mitogillin and alpha-sarcin. The present invention thus further discloses sites of the ribotoxin molecule that may be modified according to the present invention without substantial loss of biological activity.

Intact eucaryotic ribosomes have a sedimentation coefficient of 80S and are composed of 60S and 40S subunits. The 60S subunit contains 28S rRNA about 4700 nucleotides long. Alpha-sarcin produces a single fragment of 393 nucleotides derived from the 3'end of 28S rRNA and the cleavage produces 3'phosphate and 5'hydroxyl groups. The substrate must not be free rRNA since with free 28S rRNA the toxin causes extensive degradation of the nucleic acid. The fragment can also be generated from intact 80S ribosomes but not from the 40S ribosomal subunit. Due to the extremely selective action of this class of ribotoxins the structure has been highly conserved. The ability to cleave a single phosphodiester bond of 28S rRNA in a 60S ribosomal subunit may be assayed according to the method of Endo, Y. & Wool, I. G. (1982), J. Biol. Chem. 257, 9054–9060. Preferably the protein analogue has at least 5% of the potency of the native sequence ribotoxin, more preferably the protein analogue has at least 10% of the potency of the native sequence ribotoxin and especially the protein analogue has at least 12% of the potency of the native sequence ribotoxin. Potency is determined by inhibition of protein synthesis according to section 8 below.

The term "one cysteine available for covalent linkage" as used herein means that whilst the protein analogue may or may not contain other cysteines only one is readily capable of forming the covalent linkage to a partner using conjugation techniques known in the art. Usually the native ribotoxin contains other cysteines not readily available for covalent linkage to a partner. Cysteines not available for covalent linkage to a partner may for example be part of disulphide bridges or buried within the centre of the protein or within deep surface clefts. Preferably the one cysteine available for covalent linkage is present on the surface of the protein and preferably positioned away from any region associated with biological activity of the protein such as for example the active site.

"Partner" refers to a molecule which may be an individual molecule or part of a macromolecule, polymer or solid phase. Preferably the partner is an agent that selectively binds to tumours such as for example immunoglobulin or interleukin 2, more preferably a protein which selectively binds to tumours, more preferably an immunoglobulin which selectively binds to tumours and especially an immunoglobulin class G which selectively binds to tumours. A preferred antibody for selectively binding to colorectal rumours is monoclonal antibody C242 as described in international patent application WO 92/01470. "Immunoglobulin" and "antibody" refer to whole molecules as well as fragments thereof, for example known fragments such as for example Fab, Fv and single chain Fv (Methods in Enzymology 178, Academic Press 1989 and Bio/Technology 9, 545-551, 1991).

The term "native ribotoxin" includes ribotoxins as found in nature or recombinant versions thereof and analogues of such ribotoxins which have no cysteines available for covalent linkage to a partner or more than one cysteine available for covalent linkage to a partner. Preferable native ribotoxins are restrictocin, mitogillin and alpha-sarcin, more preferably restrictocin and mitogillin and especially restrictocin. The protein analogue may be derived from the native ribotoxin or from another analogue of the native ribotoxin by recombinant DNA techniques such as for example by site directed mutagenesis. For example if the native ribotoxin comprises more than one cysteine available for covalent linkage then the derivation of the analogue will involve removal of cysteines until only one remains. Preferably on the other hand if the native ribotoxin comprises no cysteines available for covalent linkage then the derivation of the analogue will involve addition of a cysteine. Removal or addition of a cysteine may involve substitution of an existing amino acid of the native ribotoxin. Thus a cysteine available for covalent linkage may be added by substitution of one cysteine in a non-essential disulphide bridge leaving the other cysteine available for covalent linkage to a partner. In general however disulphide bridges do not represent a preferred substitution site. A cysteine may also be added by an extension to the N or C terminus of the native ribotoxin or from another analogue of the native ribotoxin preferably of 1-50 amino acids, more preferably 1-40 amino acids, more preferably 1-30 amino acids, more preferably 1-20 amino acids, more preferably 1-10 amino acids, more preferably 1-5 amino acids and especially 2 amino acids. The protein analogue may also be prepared via total gene synthesis from oligonucleotides. Oligonucleotide synthesis has been reviewed by M. J. Gait in Oligonucleotide Synthesis, IRL Press 1984. Total gene synthesis has been described by H. Edwards in International Biotechnology Lab. 5(3) 19-25, 1987.

Preferred restrictocin analogues comprise:
i) restrictocin analogues in which any one of the following residues in native restrictocin comprises cysteine: Lys 13, Lys 20, Lys 28, Lys 60, Lys 63, Lys 69, Ser 82, Lys 88, Lys 106, Lys 110 and Lys 128; and
ii) native restrictocin comprising the C-terminus extension Cys 150-Gly 151; and
iii) native restrictocin comprising the N-terminus extension Gly-Cys restrictocin.

Especially preferred restrictocin analogues comprise:
i) restrictocin analogues in which any one of the following residues in native restrictocin comprises cysteine: Lys 13, Ser 82, Lys 106 and Lys 110; and
ii) native restrictocin comprising the C-terminus extension Cys 150-Gly 151.

Preferred mitogillin analogues comprise:
i) mitogillin analogues in which any one of the following residues in native mitogillin comprises cysteine: Lys 13, Lys 20, Lys 28, Lys 60, Lys 63, Lys 69, Ser 82, Lys 88, Lys 106, Lys 110 and Lys 128; and
ii) native mitogillin comprising the C-terminus extension Cys 150-Gly 151; and
iii) native mitogillin comprising the N-terminus extension Gly-Cys mitogillin.

Especially preferred mitogillin analogues comprise:
i) mitogillin analogues in which any one of the following residues in native mitogillin comprises cysteine: Lys 13, Ser 82, Lys 106 and Lys 110; and
ii) native mitogillin comprising the C-terminus extension Cys 150-Gly 151.

Preferred alpha-sarcin analogues comprise:
i) alpha-sarcin analogues in which any one of the following residues in native alpha-sarcin comprises cysteine: Lys 14, Lys 21, Lys 29, Lys 61, Lys 64, Lys 70, Ser 83, Lys 89, Lys 107, Lys 111 and Lys 129; and
ii) native alpha-sarcin comprising the C-terminus extension Cys 151-Gly 152; and
iii) native alpha-sarcin comprising the N-terminus extension Gly-Cys alpha-sarcin.

Especially preferred alpha-sarcin analogues comprise:
i) alpha-sarcin analogues in which any one of the following residues in native alpha-sarcin comprises cysteine: Lys 14, Ser 83, Lys 107 and Lys 111; and
ii) native alpha-sarcin comprising the C-terminus extension Cys 151-Gly 152.

According to another aspect of the present invention there is provided a conjugate comprising a partner covalently linked to a protein analogue as described above. Preferably the conjugate is an immunotoxin and especially a tumour selective immunotoxin. Preferably the conjugate has a potency, as determined by the in vitro cytotoxicity assay set out in section 9.1, of 10E-7M or less, more preferably the conjugate has a potency of 10E-8M or less and especially the conjugate has a potency of 10E-9M or less.

According to another aspect of the present invention there is provided a polynucleotide sequence capable of encoding a protein analogue as described above. The term "capable of encoding" refers to the degeneracy of the genetic code wherein some amino acids are encoded by more than one triplet of nucleotides or codon.

According to another aspect of the present invention there is provided a replicative cloning vector comprising the polynucleotide sequence described above such as for example a plasmid.

According to another aspect of the present invention there is provided a replicative expression vector comprising the polynucleotide sequence described above such as for example a plasmid.

According to another aspect of the present invention there is provided recombinant host cells transformed with a replicative expression vector as described above. The host cells may be procaryotic or eucaryotic such as for example bacterial, yeast or mammalian cells.

According to another aspect of the present invention there is provided a method of producing a protein analogue which comprises culture of the recombinant host cells described above. Recombinant restrictocin expressed in *E. coli* may be produced in either soluble form (particularly by manipulation of expression construct and growth conditions) or as insoluble inclusion bodies. Expression of eucaryotic polypeptides in *E.coli* is known in the art and has been reviewed by Marston, F. A. O. in Biochem. J. 1986, 240, 1-12 and in Methods in Enzymology 185, Academic Press 1990. Purification of proteins accumulating in soluble form may be accomplished by cell lysis (sonication or high pressure homogenisation), centrifugation, ion-exchange chromatography, gel permeation chromatography, ammonium sulphate precipitation, acid precipitation, triazine dye chromatography, in a variety of combinations. Renaturation and purification of insoluble restrictocin may be accomplished by cell lysis (sonication or high pressure homogenisation), centrifugation, washing of the pellet fraction with buffer or mild chaotropes, solubilisation in chaotropic agents (eg. 6M guanidine HCl, 8M urea, detergents etc with or without reductant being present) followed by the controlled removal of the chaotropic agent (eg. by dilution or dialysis) and formation of the disulphide bonds by oxidation reactions (eg. using dissolved air, glutathione redox buffers, etc). The resulting solubilised, renatured restrictocin may then be purified.

Alternatively restrictocin may be expressed by suitable yeast expression systems with secretion of the mature protein into the culture supernate using known techniques (Methods in Enzymology 194, Academic Press 1991 and Methods in Yeast Genetics by Rose, M. Winston, F. & Hieter, P., Cold Spring Harbour Press 1990). The expression system may incorporate yeast secretion sequences or Aspergillus secretion sequences such as for example restrictocin presequences to facilitate secretion of the active protein into the medium in an effective manner. Purification from yeast supernates may be achieved using standard methods.

According to another aspect of the present invention there is provided a pharmaceutical composition comprising a protein analogue covalently linked to a partner as an active ingredient in association with a pharmaceutical excipient or carrier. The composition will conveniently comprise an effective amount of the said active ingredient.

According to another aspect of the present invention there is provided a pharmaceutical composition comprising a conjugate as described above as an active ingredient in association with a pharmaceutical excipient or carrier. Preferably the conjugate is an immunotoxin and especially a tumour selective immunotoxin. The composition will conveniently comprise an effective amount of the said active ingredient.

Pharmaceutical compositions of the present invention may be in a variety of dosage forms. Generally, the pharmaceutical compositions of the present invention will be administered parenterally, preferably intravenously. A particular parenteral pharmaceutical composition is one which is formulated in a unit dosage form which is suitable for administration by injection. Thus, particularly suitable compositions comprise a solution, emulsion or suspension of the immunoconjugate or protein analogue linked to a partner in association with a pharmaceutically acceptable parenteral carrier or diluent. Suitable carriers or diluents include aqueous vehicles, for example water or saline, and non-aqueous vehicles, for example fixed oils or liposomes. The compositions may include agents which enhance stability. For example, the composition may include a buffer. The concentration of the active ingredient will vary, but in general, the active ingredient may be formulated at concentrations of about 1 to 10 mg/kg.

According to another aspect of the present invention there is provided a method of treatment of a tumour or tumours comprising the administration to a human or animal in need of such treatment of a pharmaceutically effective amount of a conjugate as described above. Preferably the conjugate is an immunotoxin and especially a tumour selective immunotoxin.

According to another aspect of the present invention there is provided a conjugate as described above for use as an active therapeutic substance. Preferably the conjugate is an immunotoxin and especially a tumour selective immunotoxin.

According to another aspect of the present invention there is provided the use of a protein analogue to prepare a conjugate such as for example an immunotoxin.

According to another aspect of the present invention there is provided a method of preparing a conjugate which method comprises linkage of a protein analogue as described above to a partner.

The invention will now be illustrated but not limited by reference to the following examples.

EXAMPLE 1

Protein Analogue Structure

The structures of restrictocin (SEQ ID NO:10), mitogillin (SEQ ID NO:47) and alpha-sarcin (SEQ ID NO:48) have been compared by Lamy, B. & Davies, J. in Nucleic Acids Research, 1991, 19, 1001–1006. Restrictocin is a 149 amino acid protein produced by *Aspergillus restrictus.* It contains 4 cysteine residues thought to form 2 disulphide bonds. Mitogillin is identical to restrictocin except for position 52 where serine in restrictocin is replaced by asparagine in mitogillin. Restrictocin and alpha-sarcin are about 86% homologous in their amino acid sequences. Due to the extremely selective action of this class of proteins the structure has been highly conserved.

Protein analogues of the present invention include restrictocin and mitogillin in which a C-terminal extension Cys 150-Gly 151 is added and alpha-sarcin in which a C-terminal extension Cys 151-Gly 152 is added. Protein analogues of the present invention include restrictocin and mitogillin in which Lys 13 is replaced with cysteine and alpha-sarcin in which Lys 14 is replaced with cysteine.

Protein analogues of the present invention include restrictocin and mitogillin in which Lys 106 is replaced with cysteine and alpha-sarcin in which Lys 107 is replaced with cysteine.

Protein analogues of the present invention include restrictocin and mitogillin in which Lys 110 is replaced with cysteine and alpha-sarcin in which Lys 111 is replaced with cysteine.

Protein analogues of the present invention include restrictocin and mitogillin in which Ser 82 is replaced with cysteine and alpha-sarcin in which Ser 83 is replaced with cysteine.

Regions of the proteins generally unsuitable for preparation of analogues of the present invention are outlined below. The loop formed by residues 34–43 is close to the active site region of restrictocin and hence changing Lys 42 to cysteine could result in a protein with compromised activity. Similar considerations apply to the corresponding residues in alpha-sarcin.

In addition changing the potential 'catalytic' residues His 136 and Glu 95 of restrictocin may result in an inactive protein. Substitution with cysteine residues adjacent to the existing cysteine residues in the molecule could result in the formation of incorrect disulphide bridges which, again, could lead to the formation of inactive molecular structures. Similar considerations apply to the corresponding residues in alpha-sarcin.

Substitution of residues which may be important in maintaining the overall conformation of the structure (in addition to the cysteine adjacent positions described above) could also lead to inactive protein due to deformation of the active site region or more gross conformational changes or structures which are unable to fold into an active structure. Such residues in restrictocin could include proline residues (eg. Proline 97, Pro 100, Pro 112, Pro 118, Pro 126 etc) or residues in the single alpha helix structure in the molecule (residues 15–28).

Similar considerations apply to the corresponding residues in alpha-sarcin.

EXAMPLE 2

Preparation of Genes Encoding Restrictocin Analogues

At all stages of the methodology, except where stated otherwise, standard molecular biological techniques were performed according to Maniatis, T. et al. (1989) Molecular Cloning—A Laboratory Manual, Cold Spring Harbour Press, New York.

2.1 Cloning of a Restrictocin Coding Sequence from *Aspergillus restrictus*

*Aspergillus restrictus* was obtained from the American Type Culture Collection (ATCC reference 34475). Spores of the fungus were used to inoculate medium containing 2% w/v soybean meal, 2% w/v corn meal, 1% w/v corn steep liquor, 0.5% w/v calcium carbonate, 1% w/v peptone and 0.5% v/v antifoaming agent comprising 3% w/v octadecanol in lard oil. 50 ml cultures were grown in 250 ml conical flasks, shaken at 30° C. for 48 hours.

Genomic DNA was isolated from *Aspergillus restrictus* as described below. Nine shake flask cultures as above were filtered through a 0.2 micrometer filter. Approximately 5 centimeter cubed portions of the filter retained material were spooned into liquid nitrogen and blended (10 fifteen second pulses) on the "high" setting in a Waring blender. The blended material was transferred to a beaker and the remaining liquid nitrogen allowed to evaporate. To this mixture was added 150 ml 0.3M sodium acetate, 15 ml 20% w/v sodium dodecyl sulphate and 15 ml phenol/chloroform (prepared as described in Maniatis et al, Molecular Cloning; A Laboratory Manual, Cold Spring Harbor Laboratory Press pp.458–459, 1982). The mixture was stirred for 5 minutes. The resulting emulsion was centrifuged at 20000 g for 5 minutes. DNA was precipitated from the aqueous phase by addition of ethanol (450 ml) and centrifugation at 20000 g for 5 minutes. The pellet was rinsed with 70% v/v ethanol (50 ml), dried in vacuo and resuspended in TE buffer pH8.0 (2 ml, prepared as described in Maniatis et al, Molecular Cloning; A Laboratory Manual, Cold Spring Harbor Laboratory Press p448, 1982) containing ribonuclease A (25 microliters of 100 micrograms per ml in TE as above, heated at 100° C. for 5 minutes). TE buffer consists of 10 mM Tris-HCl, 1 mM EDTA at pH 8. The resulting solution was incubated at 37° C. for 150 minutes then water (7 ml) and 3.0M sodium acetate (1 ml) was added. The DNA was precipitated by the addition of ethanol (30 ml) and centrifugation at 12000 g for 1 minute. The pellet was resuspended in 0.3M sodium acetate (10 ml) and extracted with phenol/chloroform (5 ml, as above). The resulting emulsion was centrifuged at 12000 g for 5 minutes. DNA was precipitated from the aqueous phase by addition of ethanol (30 ml) and centrifugation at 12000 g for 1 minute. The pellet was rinsed with 70% v/v ethanol (40 ml), dried in vacuo and resuspended in TE buffer pH8.0 (5 ml, prepared as described above). This *Aspergillus restrictus* genomic DNA solution was stored at −20° C.

A portion of the above generated DNA containing the coding sequence for mature restrictocin was amplified using the polymerase chain reaction as described by Kleppe et al in J. Mol. Biol., 56, 341–361, (1971), and Saiki et al in Science, 239, 487–491, (1988). The polymerase chain reaction was performed using the thermostable DNA polymerase isolated from the bacterium

*Thermus aquaticus* described by Chien et al in Biochemistry, 27, 1550–1557, (1976). Oligodeoxyribonucleotide (hereinafter referred to as oligonucleotide) primers were designed for the polymerase chain reaction according to the possible DNA coding sequences for restrictocin. This was done using the primary (amino acid sequence) structure of restrictocin reported by Lopez-Otin et al (Eur. J. Biochem. 143, p621–634). The nucleotide sequences of the oligonucleotide primers were variable at specific positions to allow for the degeneracy of the genetic code. Special features were introduced into the oligonucleotide primer sequences however such that not all possible codons for a given amino acid were present. The rationale being to maximise codon usage to those codons found in highly expressed genes of *E. coli.* This is thought to be particularly important at the 5′ end of the coding sequence. A further feature of the design of the oligonucleotide primers (not subsequently used) was to introduce the ability of the primers to generate analogues of the protein encoded by the DNA sequence bounded by the oligonucleotide primers when used in the polymerase chain reaction. A further feature of oligonucleotide primer design was the introduction of restriction enzyme recognition sequences to facilitate the cloning of polymerase chain reaction products derived from the use of the oligonucleotide primers.

Polymerase chain reaction amplification of the *Aspergillus restrictus* genomic DNA was effected by combining 1 microliter of the solution with 100 picomoles oligonucleotide primer SEQ.ID NO. 1, 116 picomoles oligonucleotide primer SEQ ID. NO. 2 and 1.25 units *Thermus aquaticus* DNA polymerase (Cetus "Amplitaq") in a 100 microliter solution that also contained (final concentrations) 100 micromolar each of the four deoxynucleoside triphosphates, dATP, dTTP, dCTP and dGTP, 1.2 mM magnesium chloride, 10 mMTris/HCl pH8.3, 50 mM potassium chloride and 0.01% w/v gelatin. This solution was overlaid with light mineral oil (Sigma) and subjected to thermal cycling. The thermal cycling comprised 10 cycles of 94° C. for 1 minute, 37° C. for 2 minutes and 55° C. for 2 minutes then 20 cycles of 94° C. for 1 minute, 60° C. for 2 minutes and 72° C. for 2 minutes and the final 72° C. incubation was extended to 5 minutes. After gel electrophoresis the main product was isolated using DEAE cellulose membrane (NA45 paper) as described in Maniatis, T. et al. (1989) Molecular Cloning—A Laboratory Manual, Cold Spring Harbour Press, New York. The method described in Maniatis is based on that of Dretzen et al. (1981) Anal. Biochem. 112, 295. NA45 paper is a DEAE cellulose membrane supplied by Schleicher and Schull.

The initial intention was to clone the PCR product into M13mp11 via PvuII and Sal I sites as the oligonucleotides SEQ. ID NOS. 1 and 2 contained these respective recognition sequences. However, sequencing of such M13 clones showed the restrictocin gene to be truncated, which was suspected and later confirmed to be due to a PvuII recognition sequence within the restrictocin gene sequence. Therefore, a second PCR reaction was performed to introduce other cloning sites into the PCR product, 5′ to the restrictocin gene. Approximately 1 microliter of eluate was reamplified, as above, with 100 picomoles each of oligonucleotide primers SEQ ID NOS. 3 and 4. The thermal cycling comprised 5 cycles of 94° C. for 1 minute, 37° C. for 2 minutes and 55° C. for 2 minutes then 25 cycles of 94° C. for 1 minute, 60° C. for 2 minutes and 72° C. for 2 minutes and the final 72° C. incubation was extended to 5 minutes. The main product was isolated after agarose gel electrophoresis using NA45 paper as described above.

This purified PCR product was digested with BamHI and SalI and ligated into SalI and BamHI cleaved M13mp11 using T4 DNA ligase. Ligation mixes were used to transfect *E.coli*, strain TG1. TG1 was supplied with the Oligonucleotide-Directed In-Vitro Mutagenesis System Version 2 supplied by Amersham (code RPN-1523) and was suitable for the site directed mutagenesis protocol described below but other M13 host strains which carry the F-pilus may also be used such as for example JM101 (ATCC No. 33876). Strain TG1 has a published genotype K12, delta(lac-pro), supE,-thi,hsdD5/F'traD36, proA+B+, lacI$_q$, lacZ delta M15 (Gibson 1984, Ph.D. Thesis, University of Cambridge, U.K.) and TG1 is freely available from for example the *E. coli* Genetic Stock Centre, Yale University, USA. Restrictocin sequences were checked using the dideoxy chain termination approach such as for example using the Sequenase version 2 sequencing kit supplied by United States Biochemicals. Initially M13 and M13 reverse sequencing primers were used (SEQ. ID nos.5 and 6). The restrictocin sequence was completed using sequencing primers with SEQ ID NOS. 7, 8 and 9. A sequence (SEQ. ID. NO. 10) coding for mature, wild-type restrictocin was finally obtained. The flanking sequences up to the BamHI and SalI cloning sites were as follows:

At the 5' end of the restrictocin coding sequence:

5'-GGATCCTGCA GCT ACT TGG ACT  (SEQ ID NO:43)

Ala Thr Trp Thr  (SEQ ID NO:44)

At the 3' end of the restrictocin coding sequence:

(SEQ ID NO:45)
CTG TGT AGC CAC TAA TAA TAG TCGAC-3'

Leu Cys Ser His End End End  (SEQ ID NO:46)

In order to make subsequent subcloning manipulation easier the M13-restrictocin clone was digested with restriction endonucleases SalI and HindIII. The small (approx 0.6 Kb) SalI-HindIII fragment from pBR322 was then cloned into the M13-restrictocin clone backbone. This had the effect of deleting the PstI recognition site adjacent to the SalI site situated 3' of the restrictocin gene.

The restrictocin coding sequence obtained was consistent with the published amino acid sequence for mature restrictocin except at position 115. The published amino acid sequence disclosed an asparagine residue at position 115 (Lopez-Otin et al (1984), 143, p621–634), but our sequenced PCR products indicated there was an aspartic acid residue (GAC) at position 115. The publication of the genomic sequence for restrictocin (Lamy, B. and Davies, J. (1991) Nucleic acids Res. 19(5), p1001–1006) supported our assignment suggesting the originally published amino acid sequence was incorrect. Hence, our restrictocin coding sequence (sequence ID no. 10) codes for the same protein as predicted for mature restrictocin from the genomic sequence. However, it should be emphasised that the nucleotide sequence was different at the 5' (and 3') ends due to the use of PCR to clone the gene.

2.2 Generation of Coding Sequences for Restrictocin Analogues

The purpose of cloning the restrictocin coding sequence into an M13 vector was to allow site-directed mutagenesis and so generate analogues with desired characteristic(s). Mutagenesis was performed using the Oligonucleotide-Directed In-Vitro Mutagenesis System Version 2 supplied by Amersham (code RPN-1523). This kit was based on the method of Sayers et al ((1988) Nucleic Acids Res., 16, p791–802). A 5'phosphorylated mutagenic oligonucleotide (see below) was annealed to the single-stranded template (the M13 restrictocin plasmid described above) and extended by Klenow polymerase in the presence of T4 DNA ligase to generate a mutant heteroduplex. Selective removal of the non-mutant strand was made possible by the incorporation of a thionucleotide into the mutant strand during the above in vitro synthesis. Cutting with a restriction endonuclease (NciI), which cannot cleave phosphorothioate DNA, resulted in generation of a nick in the template strand only. This nick presented a site for exonuclease III which was used to digest away part of the non-mutant (non-phosphorothioate) strand of the restrictocin sequence. The mutant strand was then used as a template to reconstruct the double-stranded closed circular molecule, by DNA polymerase I and T4 DNA ligase treatment, creating a homoduplex molecule. The sequence for restrictocin analogues TR3/TR4/TR5/TR6/TR1 which contained a Ser82 to Cys82 substitution/a Lys106 to Cys106 substitution/a Lys13 to Cys13 substitution/a C-terminal extension of Cys150-Gly151/a Lys 110 to Cys 110 substitution respectively was generated using 5'phosphorylated mutagenic oligonucleotides with SEQ ID NO. 13: CCGAAGCACT GCCAGAACGG C/SEQ ID NO 14: CACGACTATT GCTTTGACTC G/SEQ ID NO. 15: CTGAATCCCT GCACAAACAA A/SEQ ID NO. 16: CTGTGTAGCC ACTGCGGTTA ATAATAGTCG/SEQ ID NO. 41: TTTGACTCGT GCAAACCCAA G respectively.

EXAMPLE 3

Expression of Restrictocin and Analogues 3.1 Generation of the Restrictocin Expression Vector The generation of a restrictocin expression vector containing the lambdaPL promoter was initiated with the precursor plasmids, pICI0074 and pICI1079. Vector pICI1079 has been deposited under the Budapest Treaty at the National Collections of Industrial and Marine Bacteria Limited (NCIMB), 23 St. Machar Drive, Aberdeen, AB2 1RY, Scotland, U.K. (NCIMB No. 40370), date of deposit 19 Feb. 1991). The production of pICI0074 is described in European Patent Publication No 459630A2 published Dec. 4, 1991 and pICI1079 is also described therein.

pICI0074 and pICI1079 were digested with EcoRI and SacI. The fragments were then put into a ligation reaction, and the ligation reaction mixture used for transformation of *E. coli*. Screening by restriction mapping was used to identify the recombinant plasmid in which the lambdaPL/CI857 repressor fragment from pICI1079 is inserted into the pICI0074 backbone fragment which contains the tetracycline genes, a cer stability function, multiple restriction cloning sites and the T4 transcription terminator. A linker sequence containing a ribosome binding site sequence was cloned between the SacI and KpnI sites (ie. into the polylinker) of the above generated intermediate vector. The linker for generation of expression vector pICI 0122 (lambdaPL-RBS7) was made through hybridisation of the two 5′ phosphorylated oligonucleotides, SEQ. ID. NOS. 11 and 12:

```
CAATCTAGAG GGTATTAATA ATGTTCCCAT TGGAGGATGA TTAAATGGTA C
    TCGA GTTAGATCTC CCATAATTAT TACAAGGGTA ACCTCCTACT AATTTAC
```

The restrictocin coding sequence (SEQ. ID. No. 10) and the analogues of restrictocin described above were subcloned from the M13 restrictocin clones into lambdaPL-RBS7 using the subcloning strategy now detailed to generate restrictocin expression vectors. The vector encoding wild type restrictocin was called pICI 1453 (lambdaPL-RBS7-RES), the vector encoding the analogue with Ser82 to Cys82 substitution was called pICI 1485, the vector encoding a Lys106 to Cys106 substitution was called pICI 1486, the vector encoding a Lys13 to Cys13 substitution was called pICI 1487, the vector encoding the C-terminal extension of Cys150-Gly151 was called pICI 1488 and the vector encoding Lys 110 to Cys 110 substitution was called pICI 1472.

Initially, pICI 0122 was digested with KpnI and the overhang blunt-ended using T4 DNA polymerase. It was then further digested with XhoI (like KpnI, situated in the polylinker) before treating with calf intestinal alkaline phosphatase to prevent subsequent religation of the fragments. The M13-restrictocin clones containing either the wild type restrictocin or restrictocin analogues were digested with PstI and then the overhangs were blunt-ended with T4 DNA polymerase. Digestion by SalI released the restrictocin coding sequence. A ligation reaction was then performed to insert the restrictocin fragment into the pICI 0122 backbone. At the 5′ end of the restrictocin sequence the ligation is blunt-ended, but the SalI overhang at the 3′ end was compatible with the XhoI site. The PstI/blunt ending reaction results in the 5′ most base of the restrictocin fragment being the first base of the first codon of the restrictocin coding sequence. The KpnI/blunt ending reaction results in the 3′ end of the expression vector backbone reading ATG which was the initiation codon corresponding to the RBS sequence directly upstream. Hence the ligations resulted in fusion of restrictocin coding sequences in frame with the translation initiation codon.

3.2 Expression Studies

Initially, following characterisation, pICI1453 (lambdaPL-RBS7-RES) was transformed into E.coli MSD 462. 75 ml of M9 medium supplemented with 0.02% casein acid hydrolysate (Oxoid L41) and 15 μg/ml tetracycline was inoculated with a single colony from a fresh plate and grown overnight at 35° C. with gentle shaking. M9 medium comprises 6 g/l di-sodium hydrogen orthophosphate, 3 g/l potassium dihydrogen orthophosphate, 0.5 g/l sodium chloride, 1.0 g/l ammonium chloride, 1 mM magnesium sulphate, 0.1 mM calcium chloride, 2 g/l glucose and 4 μg/ml thiamine. The $OD_{550}$ was measured and the culture diluted with the same medium to give a 75 ml volume with $OD_{550}=0.1$. This culture was grown at 37° C. with gentle shaking until $OD_{550}=0.4$–0.6 (approx 3–4 hrs.). The incubator temperature was increased to 42° C. and growth continued for a further 3 hours, to allow induction of restrictocin expression. However, SDS-PAGE gels of whole cell lysates did not detect restrictocin expression. Subsequently, 35-S methionine pulse chase labelling was used to demonstrate that the short half life of restrictocin was drastically limiting its accumulation. We can overcome this instability problem by using the protease deficient strain MSD460. The growth and induction protocol is as for MSD462 except the M9 medium is further supplemented with 45 mg/l methionine. MSD460(pICI1453) gives restrictocin accumulation levels of 5–10% total cell protein and similar levels of restrictocin analogue accumulation are obtained with the restrictocin analogue expression vectors pICI 1485, pICI 1486, pICI 1487, pICI 1488 and pICI 1472.

Other promoter systems based on standard techniques may be used.

3.4 Derivation of MSD460 (Host Strain for Restrictocin Expression)

The lon allele was introduced into MSD 101 (*E. coli* W3110) by P1 transduction from SG20252 (Trislar and Gottesman (1984) J. Bacteriol. 160, 184–191) and selection for tetracycline resistance followed by screening for sensitivity to nitrofurantoin. SG20252 had the tetracycline resistance transposon Tn10 closely linked to the lon100 allele. Nitrofurantoin sensitivity was characteristic of ion-strains. One of the resultant clones was termed MSD310. Presence of the transposon in this strain was undesirable and a derivative lacking this element was isolated by screening for spontaneously arising clones which had lost tetracycline resistance. One of these, termed MSD413 was isolated and shown to retain nitrofurantoin sensitivity. This strain was mucoid, characteristic of $Lon^-$strains. To eliminate this phenotype which was due to over production of capsular polysaccharide phage Mu mutagenesis using a derivative of phage Mu termed Mu cts d1 ApR lac was employed. Following infection of MSD413 with Mu cts d1 ApR lac, ampicillin resistant clones were selected on L-amp plates and screened for a non-mucoid phenotype. One such clone termed MSD413*2 was isolated and shown to retain nitrofurantoin sensitivity. We have called the mutation in this strain which suppresses over production of capsular polysaccharide som-6. Presence of Mu cts d1 ApR lac in this strain is undesirable. A derivative which has lost the defective phage, but has retained som-6 was isolated by conventional heat curing and screening for loss of ampicillin resistance. One such clone, which appeared to retain som-6 and which was nitrofurantoin sensitive was termed MSD460.

On more extensive characterization, MSD460 was found to require methionine, but not histidine for growth (i.e was Met-) and was unable to grow on arabinose as sole source of carbon although it retained the ability to grow on glycerol. The most likely interpretation of these data is that MSD460 carries a deletion extending through metG and araFG at minute 45 of the *E. coli* genetic map, but which does not extend beyond the bis operon at minute 44 and the glp operon at minute 48.5.

MSD 460 has been deposited under the Budapest Treaty with the National Collection of Industrial and Marine Bacteria Limited (NCIMB), 23 St Macbar Drive, Aberdeen AB2 1RY, Scotland, United Kingdom. The accession number is NCIMB 40469 and the date of deposit was 9-Jan.-92.

EXAMPLE 4

Generation and Expression of Alpha-Sarcin Analogues 4.1 Construction of a Synthetic Gene Encoding Alpha-Sarcin The construction of a synthetic alpha-sarcin gene and its expression in E.coli has already been described (Henze et al. (1990) Eur. J. Biochem., 192, p127–131) (SEQ ID NO:48). However, following the successful expression of restrictocin intracellularly in *E.coli*, there appears no need to follow the published strategy of using secretion vectors to overcome potential toxicity problems.

The alpha-sarcin synthetic gene (coding sequence) is constructed in an identical fashion to that described in the Henze publication, except the oligonucleotide pairs used to construct the 5' and 3' ends of the gene are different and a base pair in one of the internal oligonucleotide pairs is different. Additional guidelines are given regarding synthetic gene synthesis in Edwards, M. (1987) International Biotechnology Lab 5(3), 19–25.

The oligonucleotide pairs used to construct the 5' end of the gene have SEQ ID nos. 26 and 27 (replacing oligonucleotides 1 and 2 in the publication). This oligonucleotide pair generate a PstI overhang beyond the coding sequence.

The oligonucleotide pairs used to construct the 3' end of the gene have SEQ ID nos. 28 and 29 (replacing oligonucleotides 18 and 19 in the publication). This oligonucleotide pair generates a Bam HI overhang and introduces a SalI site internal to this overhang, downstream of the alpha-sarcin stop codon.

The oligonucleotides 6 and 7 in the publication are replaced with SEQ ID nos 37 and 38. This removes the BamHI site but does not change the amino acid sequence.

The assembled gene is then cloned into the PstI and BamHI sites of M13mp10 via the above mentioned PstI and BamHI overhangs.

4.2 Generation of Coding Sequence for an Alpha-Sarcin Analogue

Analogues of alpha-sarcin are generated using the same M13-site directed mutagenesis methodology as described for restrictocin. The analogues described herein and the 5' phosphorylated mutagenic oligonucleotides used for their generation are as follows:

Lys 14 to Cys 14: seq ID no. 35
Ser 82 to Cys 82: seq ID no. 31
Lys 107 to Cys 107: seq ID no. 34
C-terminal extension of Cys 151—Gly 152: seq ID no. 36
Lys 111 to Cys 111: seq ID no. 42

4.3 Construction of Alpha-Sarcin Analogue Expression Vector and Expression

Following mutagenesis and characterisation, the alpha-sarcin analogue is then cloned into the expression vector, pICI0122 (LambdaPL-RBS7) as described for restrictocin and its analogues. In summary, the M13—alpha-sarcin analogue clone is digested with PstI, blunt-ended with T4 DNA polymerase, and then digested with SalI. pICI0122 is cut with KpnI, blunt-ended with T4 DNA polymerase and then digested with XhoI. A ligation reaction is then performed to introduce the alpha-sarcin coding sequence into the opened vector polylinker. This results in the ATG initiation codon in the vector being fused blunt ended and in-frame with the first codon of alpha-sarcin.

The alpha-sarcin expression vector is then intoduced into the protease defiecient strain MSD460 and induction of expression performed as described above for restrictocin and analogues.

EXAMPLE 5

Growth of *E.coli* in Fermenters and Expression of Restrictocin and Restrictocin Analogues

*E.coli* strain MSD460 was transformed with plasmid pICI 1453 and the resultant recombinant purified and maintained in glycerol stocks at −80° C. An aliquot of the culture was removed and streaked onto agar plates of L-tetracycline to separate single colonies after overnight growth at 37° C. A single colony of MSD460 pICI1453 was removed and resuspended in a 10 ml L-tetracycline broth and 100 μl immediately inoculated into each of 10 250 ml Erlenmeyer flasks containing 75 ml of L-tetracycline broth. After growth for 16 h at 37° C. on a reciprocating shaker the contents of the flasks were pooled and used to inoculate a single fermenter containing the growth medium described below.

The fermentation was carried out at a temperature of 37° C. and pH was controlled at 6.7 by automatic addition of 6M sodium hydroxide solution. The dissolved oxygen tension (dOT) set-point was 50% air saturation and was contolled by automatic adjustment of the fermenter stirrer speed. Air flow to the fermenter initially 20 L/min (corresponding to 1 volume volume per minute (VVM)) was increased to 2.5 VVM when the fermenter stirrer speed reached approximately 80–90% of its maximum. A solution of yeast extract was fed into the fermenter at a rate of 1.7 g/L/h from 4.5 h post inoculation until the culture $OD_{550}$ reached 50 when it was increased to 3.4 g/L/h.

Between 7–8 h post fermenter inoculation, when the supply of carbon source (glycerol) in the fermentation became exhausted leading to a rapid rise in dOT from 50% air saturation, a feed containing glycerol (714 g/L) and ammonium sulphate (143 g/L) was pumped into the fermenter at a rate which restricted the bacterial oxygen uptake rate (OUR) to approximately 80% of the maximum oxygen transfer rate (OTR) of the fermenter (under the conditions described). The culture was induced by raising the fermentation temperature from 37° C. to 42° C. when the culture reached an $OD_{550}=80$. The fermentation was maintained at 42° C. for 5 h. The bacteria were harvested in 1 L centrifuge bottles in a Sorvall RC-3B centrifuge (7000× g, 4° C., 30 min) and the cell paste stored frozen at −80° C.

An essentially identical protocol was followed for growth of *E.coli* strains expressing restrictocin analogues.

| Growth medium | g/L (deionized water) |
|---|---|
| Potassium dihydrogen orthophosphate | 3.0 |
| di-Sodium hydrogen orthophosphate | 6.0 |
| Sodium chloride | 0.5 |
| Casein hydrolysate (Oxoid L.41) | 2.0 |
| Ammonium sulphate | 10.0 |
| Glycerol | 35.0 |
| Yeast extract (Difco) | 20.0 |
| Magnesium sulphate 7-hydrate | 0.5 |
| Calcium chloride 2-hydrate | 0.03 |
| Thiamine | 0.008 |
| Iron sulphate 7-hydrate/Citric acid | 0.04/0.02 |
| Trace element solution (TES)* | (0.5 ml/L) |

| -continued | |
|---|---|
| Tetracycline | (10 mg/L) |

| *Trace element solution | mg/10 ml (deionized water) |
|---|---|
| $AlCl_3.6H_2O$ | 2.0 |
| $CoCl_2.6H_2O$ | 0.8 |
| $KCr(SO_4)_2.12H_2O$ | 0.2 |
| $CuCl_2.2H_2O$ | 0.2 |
| $H_3BO_3$ | 0.1 |
| KI | 2.0 |
| $MnSO_4.H_2O$ | 2.0 |
| $NiSO_4.6H_2O$ | 0.09 |
| $Na_2MoO_4.2H_2O$ | 0.4 |
| $ZnSO_4.7H_2O$ | 0.4 |

EXAMPLE 6

Purification of Protein Analogues

E.coli paste was resuspended in lysis buffer (1 g of wet cell paste per 10 ml buffer) using a homogeniser (Polytron). Lysis buffer comprises 50 mM Tris (hydroxymethyl) aminomethane hydrochloride, 2 mM (ethylenedinitrilo)tetraacetic acid (abbreviated EDTA), 0.02% Sodium azide, pH8.2. The resuspended cells at 4° C. were then lysed by high pressure homogenisation (4 passes through Manton Gaulin homogeniser) or sonication (5×45 sec bursts) and the resulting lysed cell suspension centrifuged at 25,000 g for 20 minutes.

The pH of the supernatant containing soluble toxin was adjusted to pH 7 by the addition of dilute hydrochloric acid, loaded onto a carboxymethyl ion exchange column (such as carboxy methyl Sepharose fast flow from Pharmacia) pre-equilibrated in 50 mM Tris/HCl, 2 mM EDTA, 0.02% Sodium azide, pH 7. The column was eluted with a linear gradient of 0–1M sodium chloride in the same buffer used for equilibration of the column. The elution position of the toxin was determined by analysing the column fractions by SDS-PAGE and fractions containing the toxin were pooled.

Pooled fractions were buffer exchanged into 25 mM sodium phosphate pH 7.5 by dialysis or diafiltration, toxin samples which gave a precipitate after dialysis were centrifugation at 40,000 g for 20 minutes and the supernatant collected The toxin solution was loaded onto a dye affinity column (such as mimetic green A6XL from ACL, Cambridge,U.K.) pre-equilibrated in 25 mM Sodium phosphate pH 7.5, and the flow through solution collected.

The column was washed with 25 mM sodium phosphate pH 7.5 and the wash solution collected. Contaminating proteins bound via adsorption to the dye ligand, the bulk of the toxin remained unbound and eluted in the flow through and wash. The elution position of the toxin was determined by analysis of the column fractions by SDS-PAGE and toxin containing fractions pooled.

The pooled toxin containing fractions were judged >95% pure by SDS-PAGE. A small amount of disulphide bonded toxin dimer of molecular weight 34 kDa was observed in some of the purified analogues (TR15%, TR4<5%, TR5<5%, TR6 20%). The identity of the 34 KDa band was confirmed by SDS-PAGE electroblotting and N-terminal sequencing (Problott, Applied Biosystems, USA) [Matsuidara, J.Biol. Chem 262: 10035–38].

To confirm the purity of the purified toxin aliquots of the pooled fractions were subjected to SDS-PAGE and electroblotted. The 17 kDa band was excised and subjected to N-terminus sequence analysis on an Applied Biosystems 475 protein sequencer (Applied Biosystems, USA). TR1, TR3 and TR4 gave the N-terminal sequence of restrictocin with no other detectable sequences. TR5 and TR6 gave N-terminal restrictocin sequence along with that of another unidentified protein. Searches of Genembl, Swissprot and NBRF sequence databases failed to find any significant homologies to known proteins. This contaminant was shown to represent 10 % and 15% of the total protein for TR5 and TR6 respectively, as determined by reverse phase HPLC monitored at 214 nm and comparison of the peak areas. The identities of the peaks was confirmed by N-terminal sequencing.

6.1 Detailed Experimental Protocol for Purification of Analogue TR4

200 g of analogue TR4 E. coli paste was resuspended in 2 L of lysis buffer (1 g per 10 ml) and lysed by sonication as described in section 6. 1.8 L of the lysis supernatant following centrifugation and adjustment to pH 7 as described in section 6 was loaded onto a carboxymethyl Sepharose fast flow column (Pharmacia), [column bed volume 290 mls, dimensions 5 cm i.d.×15 cm] at a flow rate of 8 mls a minute. After washing the column with the equilibration buffer until the absorbance as monitored at 280 nm returned to baseline the toxin was eluted with a linear gradient of 0–1M sodium chloride (total volume 500 mls) at 8 mls a minute. The toxin containing fractions were identified by SDS-PAGE analysis of aliquots of the fractions.

The toxin containing fractions were pooled (total volume 90 mls) and dialysed (Spectrapor 3.5 KDa cut off membrane, Pierce, U.S.A.) against 5 L of buffer as described in section 6. The dialysed toxin solution was loaded onto a mimetic green A6XL column (ACL, Cambridge, U.K.) [column bed volume 150 mls, dimensions 2.6 cm i.d.×28 cm] at a flow rate of 4.25 mls a minute and the flow through and wash collected as described in section 6. The toxin containing fractions were identified by SDS-PAGE analysis of the fractions and pooled.

Samples of the pooled purified toxin were analysed by SDS-PAGE, SDS-PAGE electroblotting and N-terminal sequencing, amino acid analysis and for biological activity in the protein synthesis inhibition assay as described in section 8.

The purified toxin was judged >95% pure by SDS-PAGE, with <5% disulphide bonded dimer, and the 17kDa SDS-PAGE blotted band gave only the N-terminal sequence of restrictocin. The yield was 7.2 mg of toxin as measured by amino acid analysis. The specific biological activity of the toxin is shown in section 8.3.

The concentration of the final purified restrictocin analogues was determined by amino acid analysis. The purified analogues were concentrated using membrane filtration before conjugation to antibody.

Samples of the purified analogues were assayed for protein synthesis inhibition activity as documented in section 8 below.

Toxin analogues TR1, TR3, TR5 and TR6 were purified and analysed using the procedures described for analogue TR4.

6.2 Purification of Recombinant Restrictocin

Recombinant restrictocin was purified as described for analogue TR4 except that the pH of the lysis supernatant was adjusted to 8 prior to loading on the carboxymethyl Sepharose fast flow column, the column was equilibrated and washed in pH 8 buffer, and the toxin eluted with a linear gradient of 0–0.5M sodium chloride in the same buffer. Also an additional column step was used after the dye affinity column, the pooled toxin containing fractions were concentrated by ultrafiltration (Amicon stirred cell YM2 membrane) and chromatographed on a Sephacryl S-200 HR size exclusion column. The column was pre-equilibrated with 20 mM sodium phosphate, 150 mM sodium chloride, pH 7.5 and the sample eluted with the same buffer. The elution position of the toxin was determined by SDS-PAGE analysis of column fractions.

The purified restrictocin eluted with and apparent molecular weight of about 17 kDa, appeared >98% pure by SDS-PAGE and the SDS-PAGE blotted band gave the N-terminal sequence of restrictocin with no other detectable sequence.

EXAMPLE 7

Conjugation of Toxin Analogues to Antibody

Monoclonal antibody, such as for example the 19.9 antibody obtained from hybridoma 1116NS-19 (ATCC No. HB 8059), in PBS at 12 mg/ml was diluted with 0.5 vols of borate buffer (100 mM sodium borate, pH 9.1). The protein concentration was determined by monitoring absorbance at 280 nm and the pH of the mixed solution noted (pH=8.7 to 8.9, preferably pH 8.8).

Linker (N-succinimidyl 3-(2-pyridyldithio) butyrate) was dissolved in dry, redistilled dimethylformamide or acetonitrile at a concentration of 10 mg/ml and added immediately to the antibody solution, with mixing, at a ratio of 8 moles linker/mole antibody. The resulting solution was incubated at 20° C. for one hour and applied to a size exclusion desalting column equilibrated with 50 mM sodium phosphate/150 mM sodium chloride/1 mM EDTA pH 8.0 to remove excess reagents and buffer exchange the derivatised antibody. The desalted derivatised antibody was pooled and protein concentration determined by monitoring the absorbance at 280 nm. The extent of derivatisation with linker was determined by addition of excess dithiothreitol to a sample of the derivatised antibody and monitoring release of free thiopyridyl groups spectroscopically at 343 nm. The extent of derivatisation was in the range 3 to 6 moles (preferably about 4 moles) linker groups per mole of antibody.

Recombinant toxin analogue was conjugated to derivatised antibody by mixing recombinant toxin analogue solution (in PBS adjusted to pH 8.0 with sodium hydroxide) and derivatised antibody solution at a 1:1 w/w toxin analogue/derivatised antibody ratio. The vessel was purged with argon and incubated at 15° C. for 40 h.

The protein solution was diluted with an equal volume of PBS adjusted to pH 8.0 with sodium hydroxide and cysteine added to a final concentration sufficient to cap excess linker groups on the antibody without reducing the disulphide bond linking the toxin to the derivatised antibody. Completion of the cysteine capping reaction was confirmed by treating a sample of the capped immunoconjugate with excess dithiothreitol and monitored spectrophtometrically at 343 nm. No release of thiopyridyl groups was detected.

The immunoconjugate solution was concentrated by membrane filtration and applied to a size exclusion chromatographic column equilibrated with 50 mM sodium phosphate/25 mM sodium chloride/1 mM EDTA, pH6.3 and having a fractionation range of 10–200 kd. The peak of protein containing immunoconjugate was pooled and the protein concentration monitored by absorbance at 280 nm.

EXAMPLE 8

Biological Assay for Ribotoxin Analogues

The aim was to establish conditions under which samples could be tested for biological activity in a cell-free in vitro protein synthesis assay.

Rabbit reticulocyte lysates were prepared according to the method of Allen and Schweet (J Biol Chem (1962), 237, 760–767). The assay demonstrates inhibition of protein synthesis in a cell-free system by a lack of incorporation of $^{14}C$-labelled leucine into newly synthesised protein.

8.1 The Assay Protocol

Stock solution: 1 mM amino acid mix minus leucine. A solution containing all L-amino acids at 1 mM except leucine (adjusted to pH7.4 with NaOH and stored at −70° C.).

Soln. A
40 mM Magnesium acetate
2M Ammonium acetate
0.2M Tris
(pH 7.4 with HCl, stored 4° C.)

Soln. B
adenosine triphosphate (Sigma A5394) 246 mg/ml
guanosine triphosphate (Sigma G8752) 24.4 mg/ml Assay mix:
1 ml Amino acid mixture
1 ml Soln. A
0.1 ml Soln. B
103 mg Creatine phosphate
1 mg Creatine kinase
510 μl H$_2$O
600 μl (60 μCi) L-$^{14}C$-leucine (New England Nuclear, NEC-279E)

Reaction mix:
Test sample 25 μl
Assay mix 12.5 μl
Rabbit reticulocyte lysate 25 μl Blank solution is 2 mg/ml bovine serum albumin(BSA) in phosphate buffered saline(PBS)

All assays were performed in duplicate 12.5 μl of assay mix placed in sterile glass tubes 25 μl of BSA in PBS added to each of first four tubes for blanks 25 μl of test samples added to rest of tubes 1 ml 0.1M potassium hydroxide added to first two tubes (background blank)

Tubes equilibrated to 28° C. in a water bath

25 μl of rabbit reticulocyte lysate (allowed to thaw from liquid nitrogen temperature) were added to each tube at 20 second intervals. When first tube had incubated for 12 minutes, 1 ml 0.1M KOH was added to each tube again at 20 second intervals to allow all tubes to have 12 minutes incubation. Two drops of 20% hydrogen peroxide were added to each tube followed by 1 ml of 20% trichloroacetic acid (TCA). Tubes were mixed and allowed to stand for at least 1 hour, or overnight, at 4° C. The precipitates were filtered on to 2.5 cm glass fibre circle (GFC) discs, washed with 3×4 ml of 5% TCA, transferred to scintillation vials and 10 ml scintillant (Ready-Solv. MP, Beckman) added. After 1 hour the vials were shaken and counted.

8.2 Establishment of Technique for use with *E.coli* Lysates 10 ml L-broth overnight cultures are grown at 37° C. 400 μl aliquots are pelleted at 13000 rpm for 30 seconds and most of the supernate decanted.

The pellets are subjected to 2 rounds of rapid freezing in solid carbon dioxide/ethanol followed by thawing at 37° C. 12 μl of 25% sucrose in 50 mM Tris HCl pH8.0 is added followed by 4 μl of a 10 mg/ml solution of lysozyme.

After incubation on ice for 15 minutes, 8 μl of 0.25M EDTA is added and incubation continued for 15 minutes. Lysis is brought about osmotically by diluting the samples to 400 μl with water. This procedure produces viable cell counts of 80–100 per ml.

When a 25 μl aliquot of this lysate is added into the assay reaction mix, the level of incorporation of $^{14}$C-leucine into newly synthesised protein is ~10% of the blank without lysate. The result clearly showed that a minimum 16-fold dilution was necessary to reduce the effect of the lysate to equal that of the blank.

In order to be as confident as possible that lysis of *E.coli* and *E.coli* lysates would not compromise ribotoxin toxicity, 2 control assays were performed. The first added ribotoxin to a 16X diluted *E.coli* cell pellet so as to give a final concentration of 8 ng/ml in the assay mix after cell lysis. Both these controls showed no deleterious affect from the lysates or the lysis procedure on the inhibitory action of ribotoxin.

These techniques were used to verify the synthesis of biologically active protein analogue.

8.3 Bioactivity of Purified Restrictocin Analogues

| Analogue | mean IC50 (M × 10E-11) | |
|---|---|---|
| TR1 | 41.1 | s.d 14.3 (n = 6) |
| TR3 | 10.5 | s.d 4.7 (n = 7) |
| TR4 | 10.8 | s.d. 4.5 (n = 6) |
| TR5 | 13.4 | s.d. 6.2 (n = 6) |
| TR6 | 4.95 | s.d. 0.68 (n = 4) |
| Recombinant Restrictocin | 2.27 | s.d 1.04 (n = 6) |

Each IC50 was calculated from a line defined by triplicates of 5 dilutions of ribotoxin wherein the calculated IC50 was greater than at least 1 of the dilutions and also less than at least 1 of the dilutions. That is to say the IC50 was calculated from a line defined by the 5 dilutions without recourse to extrapolation.

The figures for the specific activity of analogues TR5 and TR6 were corrected for 10% and 15% contaminating protein respectively in the purified product assuming that the contaminating protein had no activity in the protein synthesis assay. Other analogues tested contained no significant contamination. Restrictocin analogues TR5 and TR6 were separated from contaminants by reverse phase HPLC analysis and absorbance of the eluate monitored at 214 nm. Resulting peaks were identified by N-terminal sequencing. Percentage contamination was calculated by measurement of areas under the respective peaks.

Thus analogues TR1, TR3, TR4, TR5 and TR6 retain 6%, 22%, 21%, 17% and 46% of the potency of native sequence recombinantly produced restrictocin respectively. However this test is not conclusive of the utility of the protein analogues since the in vitro cytotoxicity assay documented below is used to test utility as an immunotoxin conjugate. For example the potency of analogue TR1 relative to native recombinant restrictocin is significantly improved in the in vitro cytotoxicity test.

EXAMPLE 9

Cytotoxicity of Immunotoxin 9.1 In vitro Cytotoxicity

This test shows the in vitro cytotoxicity of the immunotoxin against a human colo-rectal tumour cell line (Colo 205-ATCC No. CCL 222) when ribotoxin is conjugated to an antibody which recognises internalisable antigen on the cell line.

Colo 205 cells are grown in suspension in RPMI1640 medium with 2.0 g/liter sodium bicarbonate, without glutamine, with 5% heat inactivated foetal calf serum, 2 mM L-glutamine and 50 μg/ml gentamicin. The cells are trypsinised for 15 hours prior to harvesting and washing to remove trypsin. Cells are counted using haemocytometer blocks. For protein synthesis inhibition assays, cells are plated at 2–5×10$^4$ cells/well in 96 well plates in a volume of 100 μl. Immunotoxin samples are added to 4 replicate wells. Immunotoxin is added at 12 doubling dilutions from 2,000 to 0.98 ng/ml. 100 μl of culture medium is added to some wells as control. Each plate is incubated for 24 hours at 37° C., prior to 2 μCi of $^3$H-L-Leucine being added to each well. The plates are incubated at 37° C. for a further 24 hours. 50 μl of trypsin is added to each well and the plates incubated for a further 15–20 minutes. The cells are harvested from each well/plate onto glass fibre mats and radioactivity determined using an betaplate scintillation counter such as supplied by LKB. Protein synthesis inhibition curves are constructed and $IC_{50}$ values generated (see below).

| | mean IC50 (M × 10E-11) | |
|---|---|---|
| | analogue-19.9 Ab immunoconjugate | analogue alone |
| TR1 | 206 | 58300 |
| TR3 | 55.1 | 23300 |
| TR4 | 77.5 | 49800 |
| TR5 | 85.9 | 29700 |
| TR6 | 20.2 | 21700 |
| control 19.9 Ab alone | greater than 100,000 | |

Thus analogues TR1, TR3, TR4, TR5 and TR6 are useful for preparation of potent immunotoxins.

9.2 In vivo Cytotoxicity

This test shows the in vivo cytotoxicity of the immunotoxin against the human tumour cell line, COLO 205, grown as subcutaneous xenografts in athymic mice. Control groups, utilising antibody alone or phosphate buffered saline were also tested.

5×10$^6$ COLO 205 cells are injected at a single subcutaneous site in the flanks of athymic mice. Tumours are allowed to grow and measured every 3–4 days in two dimensions using calipers. Injection of test material was not initiated until tumours had reached 0.7–1.0 cm square. This stage is day 0 and test materials are injected intravenously into tail veins on day 0, 1 and 2. Tumour size continued the measured in two dimensions and presented as relative tumour volume. Measurements were made every 3–4 days until the experiment was terminated.

This test compares the effects of phosphate buffered saline, antibody alone (1.2 mg/kg) and the immunotoxin (preparation described above) (2.0 mg/kg) on rumour growth.

The immunotoxin may give rise to a reduction in tumour size in contrast to the phosphate buffered saline (PBS) control and antibody alone.

EXAMPLE 10

Composition

The following illustrates a representative pharmaceutical dosage form containing an immunoconjugate (immunotoxin) of the present invention which may be used for therapeutic purposes in humans.

Injectable Solution

A sterile aqueous solution, for injection, containing:

| | |
|---|---|
| Restrictocin analogue/tumour selective antibody | 1.0 mg |
| Sodium acetate trihydrate | 6.8 mg |
| Sodium chloride | 7.2 mg |
| Tween 20 | 0.05 mg per ml of solution |

We claim:

1. A conserved protein analogue of a native ribotoxin in which both the protein analogue and the native ribotoxin can cleave only a single phosphodiester bond of 28S rRNA in a 60S ribosomal subunit from rat liver and in which the protein analogue contains only one cysteine available for covalent linkage to a partner said cysteine not being present in the native ribotoxin wherein said peptide is selected from the group consisting of:
(a) a restrictocin analogue selected from the group consisting of:
   i) a restrictocin analogue in which any one of the following residues in native restrictocin (SEQ ID NO:10) has been substituted by cysteine: Lys 13, Lys 20, Lys 28, Lys 60, Lys 63, Lys 69, Ser 82, Lys 88, Lys 106, Lys 110 or Lys 128;
   ii) native restrictocin (SEQ ID NO:10) having additionally a C-terminus extension Cys 150-Gly 151 attached thereto; and
   iii) native restrictocin (SEQ ID NO:10) having additionally an N-terminus extension Gly-Cys attached thereto;
(b) a mitogillin analogue selected from the group consisting of:
   i) a mitogillin analogue in which any one of the following residues in native mitogillin (SEQ ID NO:47) has been substituted by cysteine: Lys 13, Lys 20, Lys 28, Lys 60, Lys 63, Lys 69, Ser 82, Lys 88, Lys 106, Lys 110 or Lys 128;
   ii) native mitogillin (SEQ ID NO:47) having additionally a C-terminus extension Cys 150-Gly 151 attached thereto; and
   iii) native mitogillin (SEQ ID NO:47) having additionally an N-terminus extension Gly-Cys attached thereto; and
(c) an alpha-sarcin analogue selected from the group consisting of:
   i) an alpha-sarcin analogue in which any one of the following residues in native alpha-sarcin (SEQ ID NO:48) has been substituted by cysteine: Lys 14, Lys 21, Lys 29, Lys 61, Lys 64, Lys 70, Ser 83, Lys 89, Lys 107, Lys 111 or Lys 129;
   ii) native alpha-sarcin (SEQ ID NO:48) having additionally a C-terminus extension Cys 151-Gly 152 attached thereto; and
   iii) native alpha-sarcin (SEQ ID NO:48) having additionally an N-terminus extension Gly-Cys attached thereto.

2. A conserved protein analogue of a native ribotoxin in which both the protein analogue and the native ribotoxin can cleave only a single phosphodiester bond of 28S rRNA in a 60S ribosomal subunit from rat liver and in which the protein analogue contains only one cysteine available for covalent linkage to a partner said cysteine not being present in the native ribotoxin
wherein said protein is selected from the group consisting of:
(a) a restrictocin analogue selected from the group consisting of:
   i) restrictocin analogues in which any one of the following residues in native restrictocin (SEQ ID NO:10) has been substituted by cysteine: Lys 13, Ser 82, Lys 106 or Lys 110; and
   ii) native restrictocin (SEQ ID NO:10) having additionally a C-terminus extension Cys 150-Gly 151 attached thereto;
(b) a mitogillin analogue selected from the group consisting of:
   i) a mitogillin analogue in which any one of the following residues in native mitogillin (SEQ ID NO:47) has been substituted by cysteine: Lys 13, Ser 82, Lys 106 or Lys 110; and
   ii) native mitogillin (SEQ ID NO:47), having additionally a C-terminus extension Cys 150-Gly 151 attached thereto; and
(c) an alpha-sarcin analogue selected from the group consisting of:
   i) an alpha-sarcin analogue in which any one of the following residues in native alpha-sarcin (SEQ ID NO:48) has been substituted by cysteine: Lys 14, Ser 83, Lys 107 or Lys 111; and
   ii) native alpha-sarcin (SEQ ID NO:48) having additionally a C-terminus extension Cys 151-Gly 152 attached thereto.

3. A polynucleotide sequence that encodes a protein analogue as defined in claim 1 or 2.

4. A replicative cloning vector comprising the polynucleotide sequence defined in claim 3.

5. A replicative expression vector comprising the polynucleotide sequence defined in claim 3 operably linked to an expression control sequence.

6. Recombinant host cells transformed with a replicative expression vector defined in claim 5.

* * * * *